(12) United States Patent
Yang

(10) Patent No.: US 7,467,551 B1
(45) Date of Patent: Dec. 23, 2008

(54) DEVICE FOR MEASURING GRIP STRENGTH

(76) Inventor: Yi-Chiang Yang, No. 57, Lane 257, Changnan Rd., Sec. 2, Changhwa (TW)

( * ) Notice: Subject to any disclaimer, the term of this patent is extended or adjusted under 35 U.S.C. 154(b) by 0 days.

(21) Appl. No.: 11/985,731

(22) Filed: Nov. 16, 2007

(51) Int. Cl.
*A63B 21/02* (2006.01)
(52) U.S. Cl. .................................................. 73/379.03
(58) Field of Classification Search ............. 73/379.01, 73/379.02; 227/120; 175/371
See application file for complete search history.

(56) References Cited

U.S. PATENT DOCUMENTS 6,053,264 A * 4/2000 Frankel et al. ............... 175/371
6,382,493 B1 * 5/2002 Cheng ......................... 227/120

\* cited by examiner

*Primary Examiner*—Jewel Thompson

(57) ABSTRACT

A device for measuring grip strength includes a shaft received in a base and a cable is wrapped on the shaft. The cable includes a first end to which the user applies a grip force and a fixed second end. A disk is connected to an end of the shaft and includes a plurality of protrusions and recesses defined between the protrusions. A detection member is located beside the disk and the protrusions pass through the detection member when the shaft is rotated by the user. A transferring unit is connected to the base and includes a fixed part and an operation unit movably connected to the fixed part. A rod is movable with the operation unit and connected to the first end of the cable. A biasing unit includes a spring which returns the rod when the user releases the rod.

6 Claims, 5 Drawing Sheets

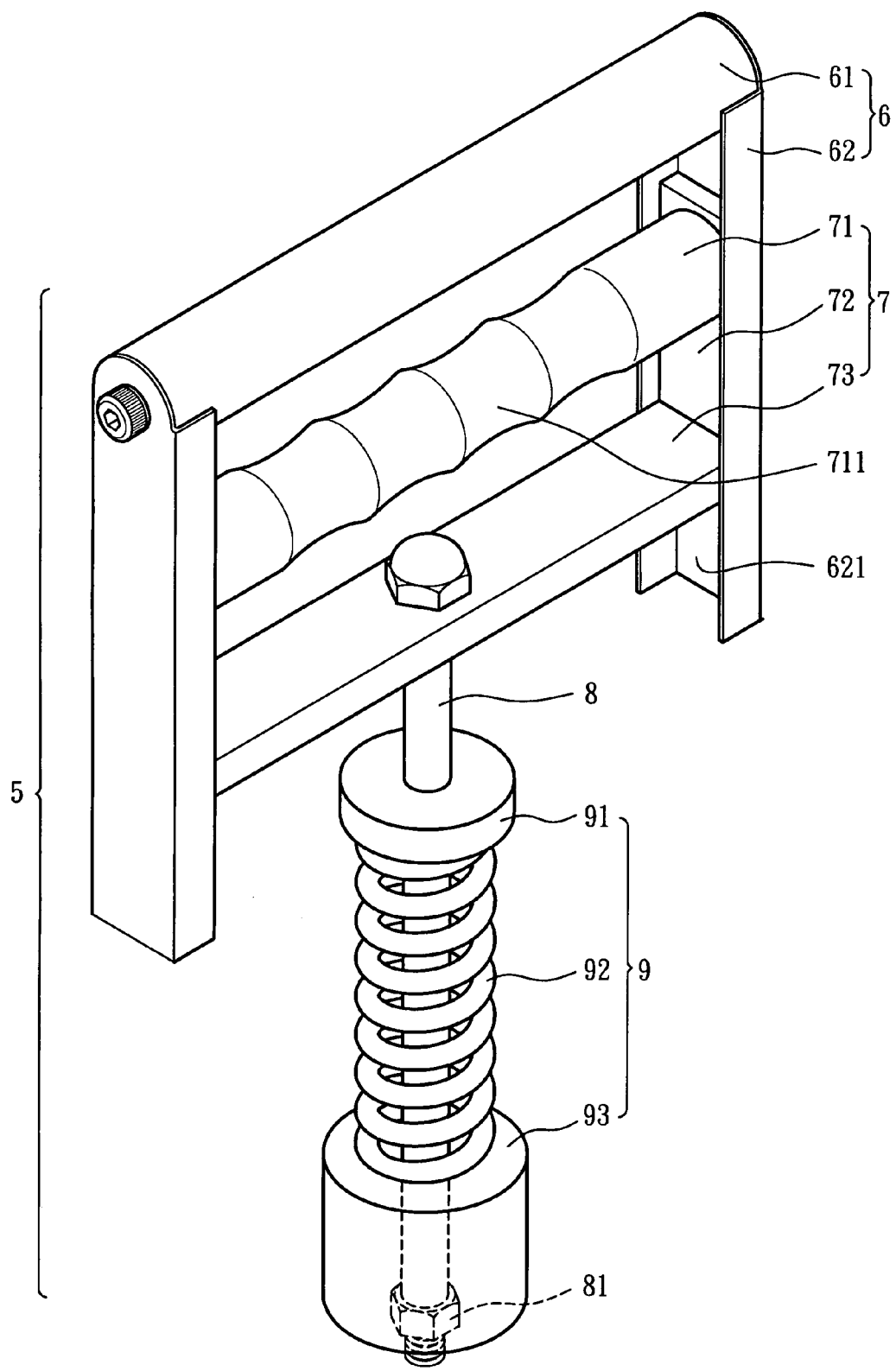
F I G . 2

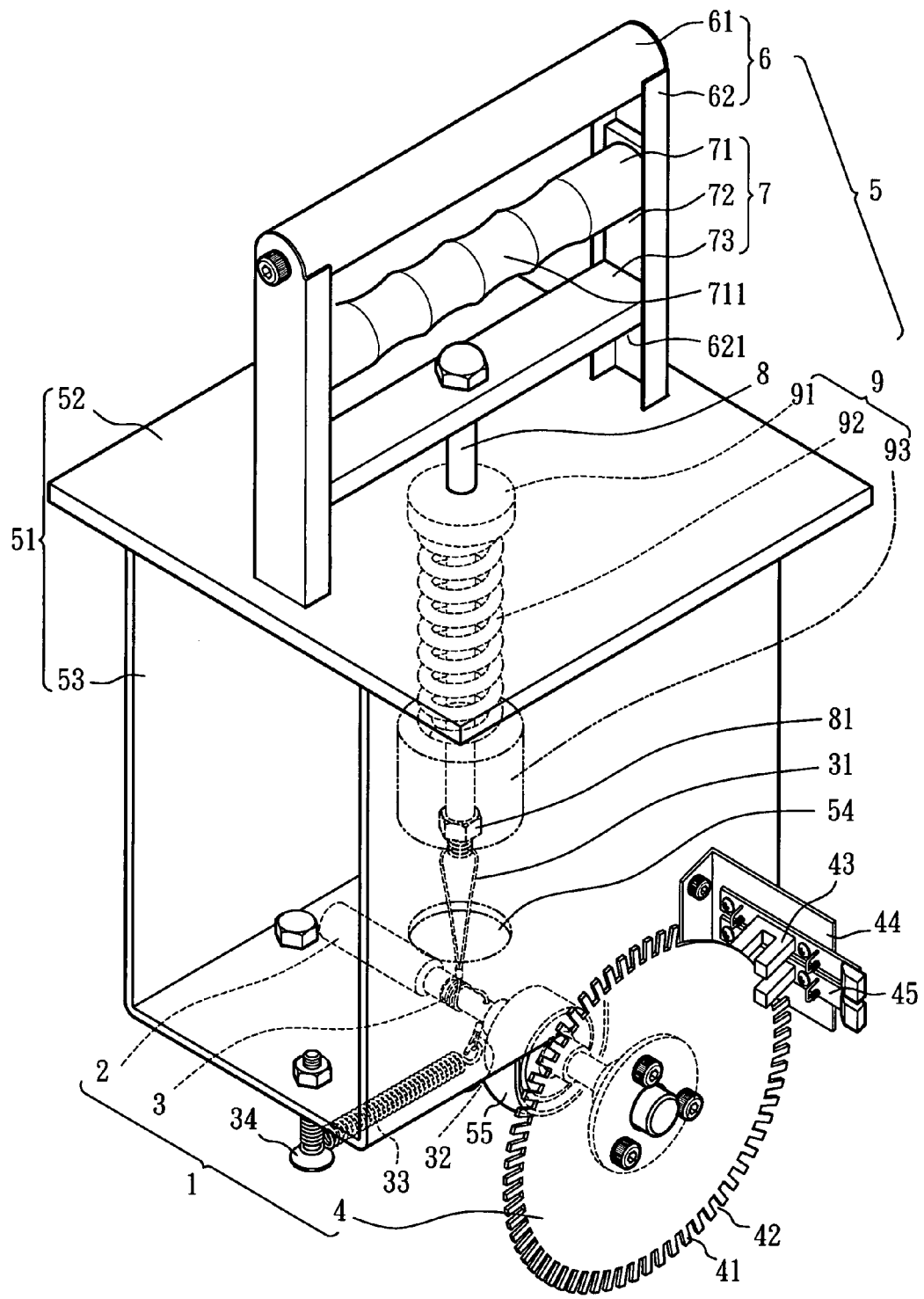
F I G . 3

DEVICE FOR MEASURING GRIP STRENGTH

FIELD OF THE INVENTION

The present invention relates to a device for measuring user's grip strength.

BACKGROUND OF THE INVENTION

A conventional device for training grip strength generally includes a biasing member and the user holds the biasing member and tries to compress the biasing member so as to exercise the muscles of hands. A conventional measuring device uses a rack to drive a gear which is connected with an arm which is pivoted to point one of the measuring marks. The user then reads the marks to obtain the data of the force that applied to the rack.

The present invention intends to provide a grip measuring device that is used as a game set and the users grip and pull the handle, a precise value of the grip strength is displayed.

SUMMARY OF THE INVENTION

The present invention relates to a device for measuring grip strength, and comprises a checking unit received in a base and a shaft is located in the base. A cable is wrapped on the shaft and includes a first end and a second end. A disk is connected to an end of the shaft and includes a plurality of protrusions extending radially outward from a periphery thereof and recesses are defined between the protrusions. A detection member is located beside the disk and the protrusions are movable through the detection member when the cable is pulled by the users. A transferring unit is connected to the base and includes a fixed part and an operation unit is movably connected to the fixed part. A rod is movable with the operation unit and connected to the first end of the cable. A biasing unit is used to return the rod.

The primary object of the present invention is to provide a grip strength detection device which includes a handle for the user to hold and apply a force, the movement of the rod drives a cable which rotates a shaft. A disk is connected to an end of the shaft and includes protrusions which pass through a photoelectric sensor so as to detect the angular distance that the disk travels. The angular distance is transferred into value of the grip strength.

The present invention will become more obvious from the following description when taken in connection with the accompanying drawings which show, for purposes of illustration only, a preferred embodiment in accordance with the present invention.

BRIEF DESCRIPTION OF THE DRAWINGS

FIG. 2 is a perspective view to show the transferring unit of the present invention;

FIG. 3 is a perspective view to show the checking unit and the transferring unit connected to the support unit of the present invention;

DETAILED DESCRIPTION OF THE PREFERRED EMBODIMENT

Figure 1:
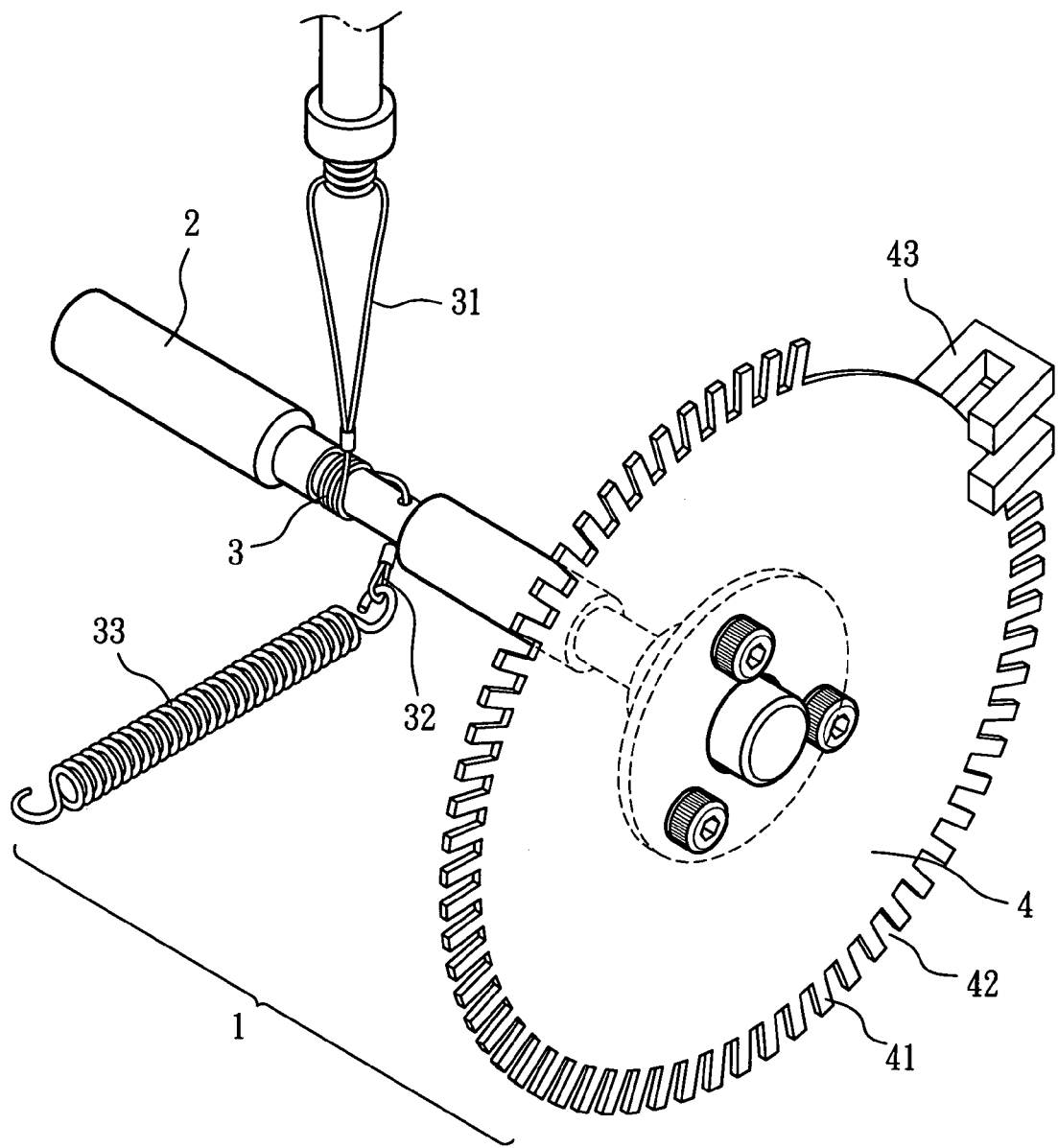
FIG. 1 is a perspective view to show the checking unit of the present invention.
Figure 4:
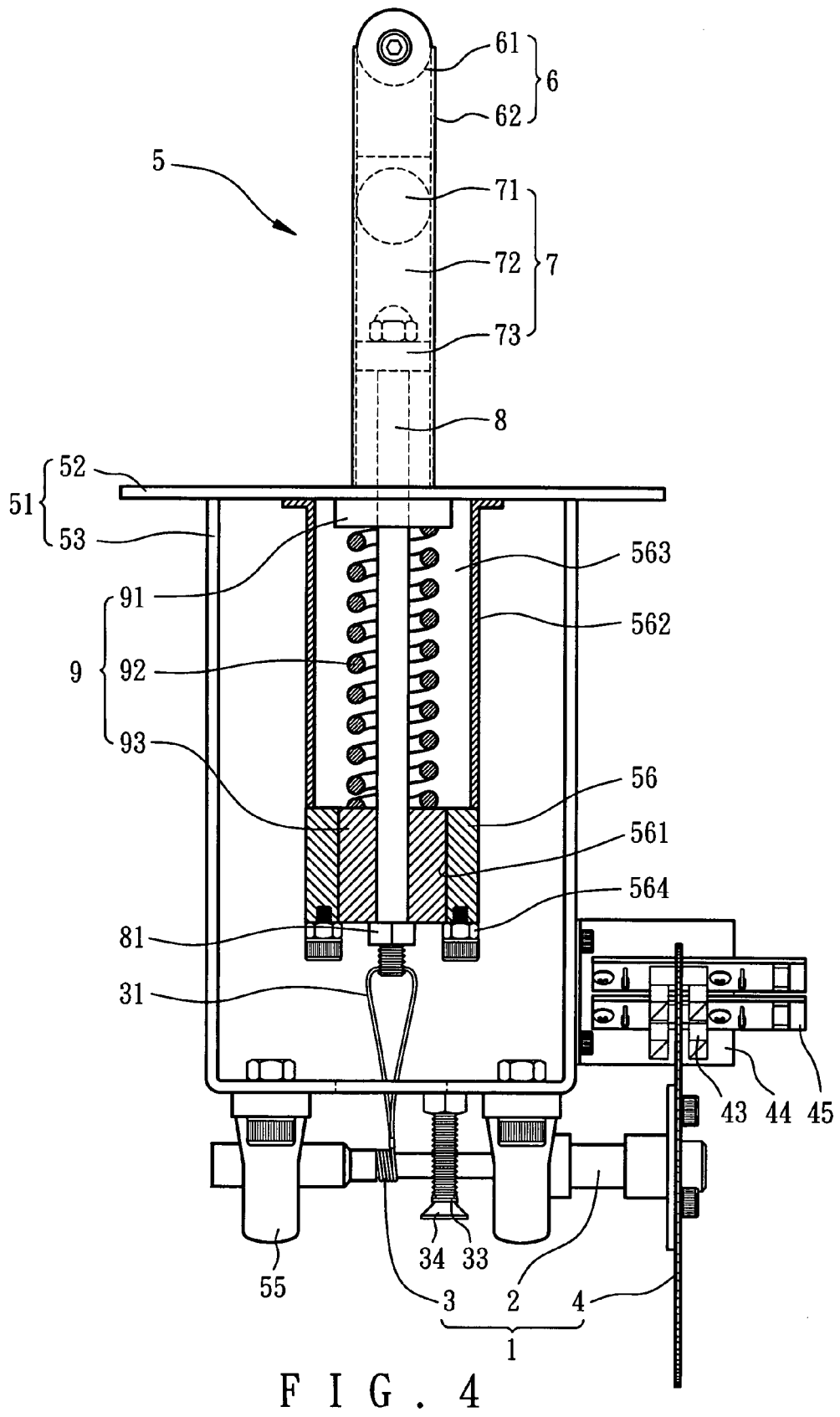
FIG. 4 is a side view to show the grip strength measuring device of the present invention.

Referring to FIGS. 1 to 4, the device for measuring grip strength of the present invention comprises a checking unit 1 received in a base 11 and the checking unit 1 includes a shaft 2. A cable 3 is wrapped on the shaft 2 and includes a first end and a second end 32 which extends through a radial hole in the shaft 2. A spring 33 has one end connected to the second end 32 and the other end of the spring 33 is fixed to a bolt 34 which is fixed to a support unit 51. A disk 4 is connected to an end of the shaft 2 and includes a plurality of protrusions 41 extending radially outward from a periphery thereof and recesses 42 are defined between the protrusions 41. A detection member 43 is connected to a circuit board 45 which is fixed on a frame 44. The detection member 43 is located beside the disk 4 and the protrusions 41 pass through the detection member 43 when the shaft 2 is rotated to drive the disk 4. The detection member 43 is a photoelectric sensor.

A transferring unit 5 is connected to the support unit 51 and includes a fixed part 6 and an operation unit 7. The support unit 51 includes a top 52 and a lower part 53 which is connected to an underside of the top 52. The lower part 53 includes a hole 54 and the first end 31 of the cable 3 extends through the hole 54. The shaft 2 is connected to a bearing 55 which is connected to an underside of the lower part 53. The fixed part 6 is connected to the top 52 and includes a top rod 61 and two sides 62. Each side 62 includes a groove 621 defined in an inside thereof and the top rod 61 is fixedly connected between the two facing grooves 621.

The operation unit 7 includes a handle 71, two blocks 72 connected between the handle 71 and a connection plate 73 which is parallel to the handle 71. The two blocks 72 are movably engaged with the grooves 621 of the two sides 62. The rod 8 has one end connected to the connection plate 73 and the other end of the rod 8 extends through the top 52 and is connected to the first end 31 of the cable 3. The biasing unit 9 includes a spring 92 and a lower member 93 which is connected with a first end of the spring 92. The spring 92 is mounted to the rod 8 and a top disk 91 is fixed on the rod 8, a second end of the spring 92 is stopped by the top disk 91 which is in contact with the top 52. The biasing unit 9 is used to returns the rod 8 when the rod 8 is released.

A cylindrical member 562 has one end connected to the underside of the top 52 and the spring 92 is received in the space 563 in the cylindrical member 562. A tube 56 is connected to the other end of the cylindrical member 562 and a passage 561 is defined through the tube 56 so that the lower member 93 is movably received in the passage 561. Two locking nuts 564 are cooperated with two bolts are connected to an underside of the tube 56 so as to restrict the lower member 93 from dropping off from the passage 561. The rod 8 includes a threaded section which extends through the lower member 93 and is connected to a nut 81. The first end 31 of the cable 3 is fixed to the threaded section.

Figure 5:
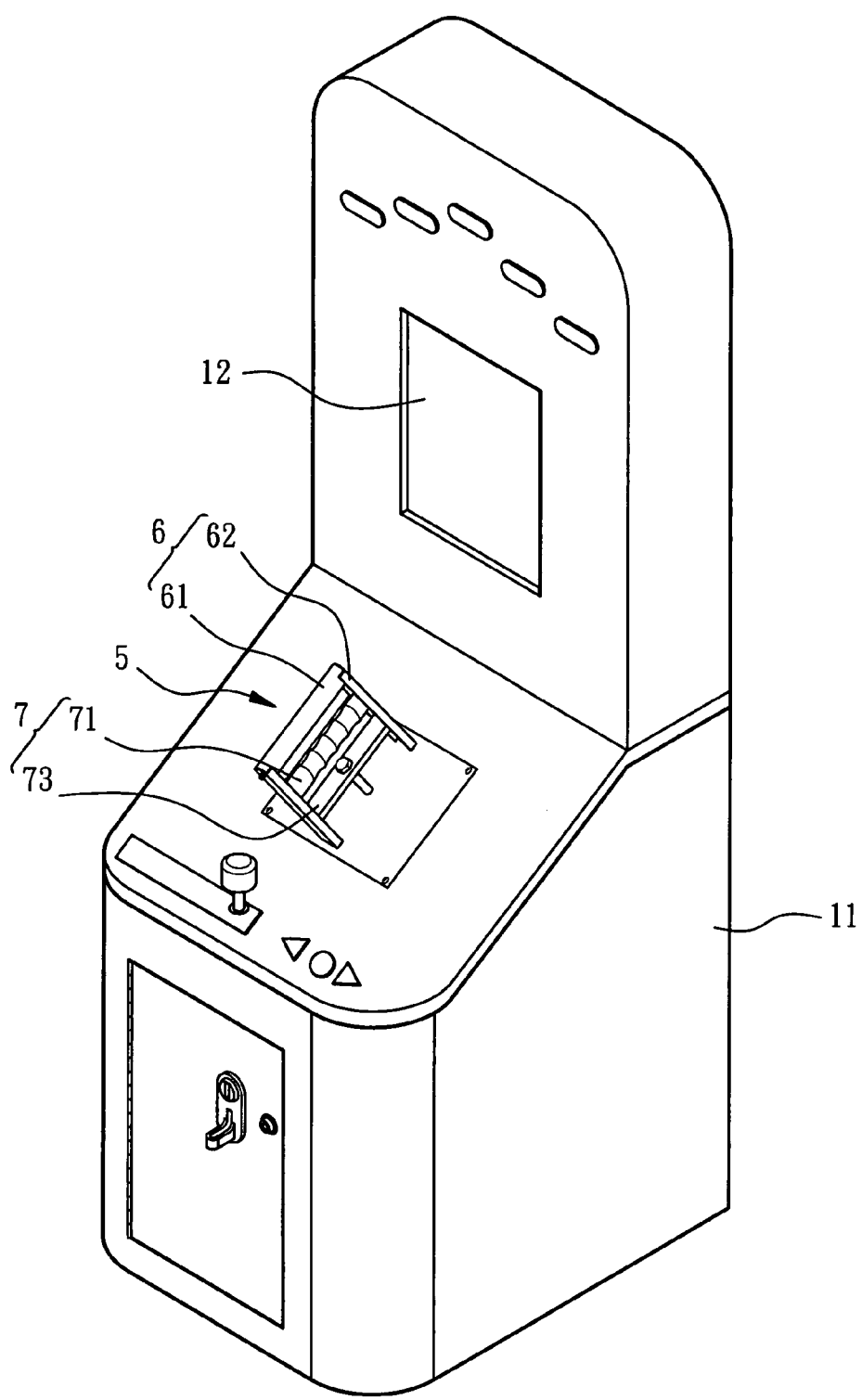
FIG. 5 shows that the grip strength measuring device of the present invention is displayed by a game set.

As shown in FIG. 5, the device can be made in a form of a game machine to attract users to play and a display screen 12 is provided to show the value of the grip strength that the user performs. The handle 71 includes several annular recesses 711 for convenient grasp by the user's hand and the user holds the top rod 61 by his/her thumb and the four fingers grasp the handle 71. The handle 71 is then pulled upward and the movement of the handle 71 pulls the cable 3 which rotates the shaft 2 which drives the disk 4. The short distance that the handle 71 moves is transferred into angular distance that the disk 4 travels, the detection member 43 detects the number of the protrusions 41 that pass through the detection member 43 within a certain period of time. The force of the grip can then be precisely measured.

While we have shown and described the embodiment in accordance with the present invention, it should be clear to those skilled in the art that further embodiments may be made without departing from the scope of the present invention.

What is claimed is:

1. A device for measuring grip strength, comprising:
a checking unit received in a base and having a shaft, a cable wrapped on the shaft and including a first end and a second end which is connected to a spring;
a disk connected to an end of the shaft and including a plurality of protrusions extending radially outward from a periphery thereof and recesses defined between the protrusions;
a detection member located beside the disk and the protrusions movable through the detection member;
a transferring unit connected to the base and including a fixed part and an operation unit movably connected to the fixed part, a rod movable with the operation unit and connected to the first end of the cable, the shaft being rotated when the operation unit is pulled to lift the rod and the first end of the cable, the disk rotated with the shaft so as to rotate the disk the detection member detecting the protrusions passing therethrough to calculate a force applied to the operation unit, and
a biasing unit 9 which returns the rod 8.

2. The device as claimed in claim 1, wherein the support unit includes a top and a lower part connected to an underside of the top, the lower part includes a hole, the shaft is connected to a bearing which is connected to an underside of the lower part, the first end of the cable extends through the hole, the fixed part is connected to the top and includes a top rod and two sides, each side includes a groove defined in an inside thereof and the top rod is fixedly connected between the two facing grooves, the operation unit includes a handle, two blocks connected between the handle and a connection plate which is parallel to the handle, the two blocks are movably engaged with the grooves of the two sides, the rod has one end connected to the connection plate and the other end of the rod extends through the top and is connected to the first end of the cable, the biasing unit includes a spring and a lower member which is connected with a first end of the spring, the spring is mounted to the rod and a second end of the spring is in contact with the top.

3. The device as claimed in claim 2, wherein a cylindrical member has one end connected to the underside of the top and a tube is connected to the other end of the cylindrical member, a passage is defined through the tube and the lower member is movably received in the passage.

4. The device as claimed in claim 1, wherein the detection member is a photoelectric sensor.

5. A device for measuring grip strength, comprising:
a checking unit received in a base and having a shaft, a cable wrapped on the shaft and including a first end and a second end which is connected to a sprint;
a disk connected to an end of the shaft and including a plurality of protrusions extending radially outward from a periphery thereof and recesses defined between the protrusions;
a detection member located beside the disk and the protrusions movable through the detection member and
the shaft being rotated when the first end of the cable is pulled by a force, the disk rotated with the shaft so as to rotate the disk, the detection member detecting the protrusions passing therethrough to calculate the force applied to the cable.

6. The device as claimed in claim 5, wherein the shaft has one end connected to a bearing which is located in the base, the second end of the cable is connected with a spring and the other end of the spring is fixed to the base, the detection member is a photoelectric sensor.

* * * * *